(12) United States Patent
Ebersbach et al.

(10) Patent No.: US 9,492,077 B2
(45) Date of Patent: Nov. 15, 2016

(54) OPTIMIZED DEVICE FOR SWEPT SOURCE OPTICAL COHERENCE DOMAIN REFLECTOMETRY AND TOMOGRAPHY

(75) Inventors: Ralf Ebersbach, Schmoelln (DE); Martin Hacker, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 90 days.

(21) Appl. No.: 13/981,688

(22) PCT Filed: Jan. 30, 2012

(86) PCT No.: PCT/EP2012/051415
§ 371 (c)(1),
(2), (4) Date: Jul. 25, 2013

(87) PCT Pub. No.: WO2012/107307
PCT Pub. Date: Aug. 16, 2012

(65) Prior Publication Data
US 2013/0308097 A1    Nov. 21, 2013

Related U.S. Application Data

(60) Provisional application No. 61/441,873, filed on Feb. 11, 2011.

(30) Foreign Application Priority Data

Feb. 11, 2011    (DE) .................. 10 2011 011 277

(51) Int. Cl.
*A61B 3/14*    (2006.01)
*A61B 3/10*    (2006.01)
*G01B 9/02*    (2006.01)

(52) U.S. Cl.
CPC ........... *A61B 3/102* (2013.01); *G01B 9/02004* (2013.01); *G01B 9/02059* (2013.01); *G01B 9/02091* (2013.01)

(58) Field of Classification Search
CPC ...... A61B 3/0025; A61B 3/102; A61B 3/14; A61B 5/0059; A61B 5/0077; A61B 5/0084; A61B 3/12; A61B 3/113; A61B 3/1225; A61B 5/01; A61B 5/7278; A61B 3/0058; A61B 5/0082; A61B 5/0816; A61B 5/14552; A61B 5/742; A61B 3/0041

USPC ........ 356/479, 497; 351/205–207, 221, 246; 600/476; 359/216.1, 201.1; 378/21–27
See application file for complete search history.

(56) References Cited

U.S. PATENT DOCUMENTS

| | | | |
|---|---|---|---|
| 5,321,501 A | 6/1994 | Swanson et al. | |
| 7,330,270 B2 | 2/2008 | O'Hara et al. | |

(Continued)

FOREIGN PATENT DOCUMENTS

| | | |
|---|---|---|
| DE | 4309056 A1 | 3/1993 |
| DE | 102008051272 A1 | 10/2008 |
| DE | 102008063225 A1 | 7/2010 |
| EP | 1 870 030 A1 | 12/2007 |
| WO | WO 2010/09447 A3 | 3/2010 |

OTHER PUBLICATIONS

Adrian GH. Podoleanu, "Fiber Optics, From Sensing to Non Invasive High Resolution Medical Imaging", Journal of Lightwave Technology, IEEE Service Center, New York, NY, US, vol. 26, No. 4, Feb. 15, 2010, pp. 624-640, XP011283126, ISSN: 0733-8724.

(Continued)

*Primary Examiner* — James Greece
*Assistant Examiner* — Sharrief Broome
(74) *Attorney, Agent, or Firm* — Patterson Thuente Pedersen, P.A.

(57) ABSTRACT

Optimized device for swept source optical coherence domain reflectometry and tomography. In the coherence-optical device, light, with the aid of an interferometer, is used for distance-measuring and imaging purposes on reflecting and scattering areas of the human eye. The optimized device according to the invention consists of includes a tunable light source, matched to the sought-after measurement region ZOCT, with a resonator length LR, an interferometric measurement arrangement, a data capturing unit for capturing the light portions scattered back from the sample and a data processing unit. Here the resonator length LR of the tunable light source is matched not only to the sought-after measurement region ZOCT, but also to the entire interferometric measurement arrangement such that disturbance points present in the interferometric measurement arrangement cannot create disturbance signals in the sought-after measurement region ZOCT.

17 Claims, 8 Drawing Sheets

(56) References Cited

U.S. PATENT DOCUMENTS

| | | | |
|---|---|---|---|
| 2006/0105903 A1 | 5/2006 | Tatsumi et al. | |
| 2006/0171503 A1 | 8/2006 | O'Hara et al. | |
| 2007/0216909 A1 | 9/2007 | Everett et al. | |
| 2007/0291277 A1* | 12/2007 | Everett | A61B 3/102 356/497 |
| 2008/0100612 A1 | 5/2008 | Dastmalchi et al. | |
| 2009/0059971 A1 | 3/2009 | Atia et al. | |
| 2009/0290167 A1 | 11/2009 | Flanders et al. | |
| 2010/0097614 A1* | 4/2010 | Kourogi | A61B 5/0066 356/477 |

OTHER PUBLICATIONS

Chong Ch., u.a.: Large coherence length swept source for axial length measurement for the eye, In: Applied Optics, 48, 2009, 10, D144-D150.

Hammer D. X.: Active Retinal tracker for clinical optical coherence tomography systems, In: Journal of Biomedical Optics, 10, 2005, 2, 024038-1-024038-11.

Hitzenberger C. K., u.a.: In vivo intraocular ranging by wavelength tuning interferometry, In: SPIE, 3251, 1998, 47-51.

Kim D. Y., u.a.: Very High Frequency Ultrasound Analysis of a New Phakik Posterior Chamber of Intraocular Lens in Situ, In: Journal of Ophthalmology, 125, May 1998, 5, 725-729.

Lexer, F. et al.: Wavelength-tuning interferometry of intraocular distances; Applied Optics, vol. 36, No. 25, 1997, 6548-6553.

Reinstein D., u.a.: Correlation of Anterior Chamber Angle and Ciliary Sulcus, In: J Refect Surg., 25, Feb. 2009, 2, 185-194.

Yun S. H.: High-speed optical frequency-domain imaging, In: Optics Express, 11, 2003, 22, 2953-2963.

Yun S. H.: Motion artifacts in optical coherence tomography with frequency-domain ranging, In: Optics Express, 12, Jun. 2007, 13, 2977-2998.

\* cited by examiner

OPTIMIZED DEVICE FOR SWEPT SOURCE
OPTICAL COHERENCE DOMAIN
REFLECTOMETRY AND TOMOGRAPHY

RELATED APPLICATIONS

The present application is a National Phase entry of PCT Application No. PCT/EP2012/051415, filed Jan. 30, 2013, which claims priority from DE Application No. 10 2011 011 277.4, filed Feb. 11, 2011 and U.S. Patent Application No. 61/441,873, filed Feb. 11, 2011, which applications are hereby incorporated by reference herein in their entirety.

FIELD OF THE INVENTION

The present invention relates to a device for swept source optical coherence domain reflectometry (SS OCDR) and tomography (SS OCT), more particularly on the human eye.

BACKGROUND

The methods and measuring equipment based on optical coherence domain reflectometry (OCDR) and optical coherence tomography (OCT) constitute the most widely-used solutions according to the known prior art for biometrically measuring and/or tomographically imaging eye structures.

In these coherence-optical methods, coherent light is, with the aid of an interferometer, used for distance-measuring and imaging purposes on reflective and scattering samples. On the human eye, the methods supply measurable signals when scanning the depth as a result of changes in the refractive index occurring at optical interfaces and as a result of volume scattering.

Optical coherence tomography is a very sensitive and quick method for interferometric imaging, which has found widespread use, particularly in the medical sector and in basic research. The images of eye structures based on OCT scans are often used in ophthalmology for diagnosis and accompanying therapy, and also for planning interventions and for selecting implants.

The basic principle of the OCT method, described e.g. in U.S. Pat. No. 5,321,501, is based on white-light interferometry and compares the run-time of a signal with the aid of an interferometer (usually a Michelson interferometer). In the process, the arm with a known optical path length (=reference arm) is used as a reference for the measurement arm, in which the sample is situated. The interference of the signals from both arms results in a pattern, from which it is possible to determine the scattering amplitudes as a function of the optical delay between the arms and hence a depth-dependent scattering profile, which, analogously to ultrasound technology, is referred to as an A-scan. In the multi-dimensional scanning methods, the beam is then guided transversely in one or two directions, as a result of which it is possible to record a two-dimensional B-scan or a three-dimensional volume tomogram. Here, the amplitude values of the individual A-scans are displayed using linear or logarithmic grayscale or false-color values. The technique of recording individual A-scans is also referred to as optical coherence domain reflectometry (OCDR), compared to which OCT realizes two- or three-dimensional imaging as a result of lateral scanning.

Two different basic types have prevailed in the OCT methods used in ophthalmology. In the first type, the length of the reference arm is changed and the intensity of the interference is recorded continuously in order to determine the measurement values, without this taking the spectrum into account. This method is referred to as a "time domain" method (U.S. Pat. No. 5,321,501 A). By contrast, in the other method, which is referred to as a "frequency domain" method, the spectrum is captured and the interference of the individual spectral components is evaluated in order to determine the measurement values.

It is for this reason that one refers firstly to the signal being in the time domain and secondly to the signal being in the frequency domain. The advantage of the "frequency domain" method lies in the simple and quick simultaneous measurement, in which it is possible to establish complete information in respect of the depth without requiring moveable parts. This increases the stability and the speed (U.S. Pat. No. 7,330,270 B2), as a result of which three-dimensional OCT recordings in particular were rendered possible.

In the case of frequency domain OCT, a distinction is furthermore made as to whether the spectral information is obtained by means of a spectrometer ("spectral domain OCT", SD-OCT) or by means of spectral tuning of the light source ("swept source OCT", SS-OCT).

A great technological advantage of OCT lies in the depth resolution being decoupled from the transverse resolution. As a result, it is possible to obtain very good axial resolutions, particularly also in the case of limited numerical apertures, such as for example in order to be able to examine retinal layers in the axial direction with high (<20 µm) and highest (<4 µm) resolutions, despite an aperture restriction by the pupil. The OCT measurement, which is based on back-scattering and reflection and hence is contactless, thus allows the generation of microscopic images of living tissue (in vivo). A further advantage lies in the efficient suppression of incoherent disturbance-light portions. In this case, the "axial direction" means the direction of the depth profile displayed in the A-scan. This direction may also vary in parts of the A-scan as a result of local refractions, but usually is almost parallel to the optical axis or to the visual axis from the corneal vertex to the fovea of an eye to be examined.

A first application of the display of the overall depth profile of the back-scattering from the eye, based on coherence-reflectometric measurements (OCDR), is described by F. Lexer et al. in [1]. Here, emphasis is once again placed on the fact that the precise knowledge of the intraocular distances is an important aid in modern ophthalmology, for example for fitting intraocular lens implants. While the axial eye length and the anterior chamber depth are mandatory for precise calculations of the refractions of intraocular lenses for cataract operations, the precise measurement of the corneal thickness is important for refractive surgery. Determining the thickness of the retinal layers can assist in diagnosing various disorders and monitoring the therapeutic effects. The approach to the solution described in [1] is based on an average-quality SS-FD-OCDR system and affords the possibility of measuring the distances of all optical areas in the eye over the whole eye length. Although it was still possible to obtain a high resolution when scanning the entire measurement region of model eyes using the approach to the solution, this was no longer possible during the simultaneous "in vivo" measurement of three intraocular distances. It was found that the approach to the solution for measuring intraocular distances with an accuracy of at best 30 µm achieves an adequate resolution; however, it is no longer suitable for high-resolution OCDR or OCT applications.

The laid-open applications US 2007/216909 A1, US 2007/291277 A1 and US 2008/100612 A1 describe SD-OCT systems which comprise a switchable focus and/or a switchable reference plane (zero-delay) of the OCT arrangement. Here, the focus should lie in the region of the retina in the case of a retinal scan and in the region of the cornea in the case of a cornea scan. Hence an OCT scan with a high lateral resolution of the anterior or posterior section of the eye is possible. Furthermore, a retinal scan with a scan rotation point in the iris/pupil plane is described as expedient. The solutions proposed here allow both high-resolution two-dimensional scans and three-dimensional scans (data cubes) to be recorded and evaluated.

A further OCT system based on the "frequency domain" is described by Walsh et al. in WO 2010/009447 A2. The spectral information is obtained either by use of a spectrometer (SD-OCT) or by use of a spectrally tunable light source (swept source, SS-OCT). Herein, the eye can be displayed in a plurality of sections along the optical axis or as a whole by application of an A-, B- or C-scan. The solution describes both a method for the whole eye scan and also partial scans arranged next to one another. The necessity of the scan rotation point being in the pupil for a retinal scan is also highlighted here. Furthermore, many ophthalmological application options for whole-eye scans are described.

The OCDR system described in DE 10 2008 051272 A1 serves for interferometrically measuring eye-section lengths over the whole eye length. A laterally scanning OCDR system is described, in which the focus too is variable or switchable in order to realize optimum A-scan signals by combination. No solution is proposed for displaying combined partial- or whole-eye OCT scans in an anatomically correct fashion. The radiation back-scattered from the interfaces of the eye is recorded by interferometry and a measurement signal displaying structures of the eye is created by time-domain, spectral-domain or Fourier-domain coherence reflectometry. This OCDR system provides a solution by which preferably a plurality of very precise partial distance measurements should simultaneously take place on the eye. The proposed OCDR system provides a solution by which eye section lengths can be measured in a very precise fashion over the entire eye length. Tomographic OCT recordings of the anterior and posterior eye sections by means of an A-, B- or C-scan are not possible using this system.

An OCDR system, which is based on long-coherent, tunable lasers (swept sources) and has over 40 mm scan depth in tissue, was proposed in DE 10 2008 063 225 A1. In particular, good signal ratios and low movement sensitivity on all interfaces of the eye can be realized well with this, even in the case of very long eyes, as is also shown in one example. An OCT system with a depth range of almost 35 mm, based on a relatively long-coherent, tunable source, is described by Ch. Chong et al. in [2]. In principle, the approach to the solution can realize tomographic images of the whole eye, in which images the contours of cornea, iris, lens and retina are rudimentarily visible. However, in the experimental implementation, it is difficult to see the details of the segments because implemented lateral resolutions and the signal strengths are rather low. As a result of the strong signal attenuation due to the insufficient coherence length of the source of only 28 mm, it was only possible to measure pig's eyes with a geometric length of approximately 20 mm. The system is inadequate for human eyes with a geometric length of up to 40 mm.

Furthermore, in [3] and [4], Reinstein et al. describe depth-resolved eye scans that can be used to display regions in the eye that cannot be displayed by means of OCT. By way of example, the prior art has disclosed highly-resolved ultrasound representations of anterior regions of the eye, including edge region of the lens of the eye behind the iris or the position of IOLs including the haptics behind the iris.

Registering OCT scans amongst one another or spatial referencing and correction by means of reference information from other, non-depth-resolving measurement systems, for example with height information of topographies, as described by Tang et al. in [3], is advantageous for the spatial assignment of measurement data. In addition to partial distance measurements, topographies or keratometries are required parameters for fitting refractive intraocular implants such as IOLs.

DE 43 09 056 describes another measurement method, based on short coherence, in which light from a broad-band light source is radiated into the sample and the light scattered back from various depths is analyzed spectrally. The depth information is obtained from a Fourier transform of the detected signal. This method is referred to as spectral domain OCDR (SD OCDR) or, since a Fourier transform is used, else as Fourier domain OCDR (FD OCDR). This category also includes the swept source OCDR (SS OCDR), as described in article [5] by S. H. Yun et al., in which the light source is spectrally tuned and the signal captured by the detector likewise contains the depth information after a Fourier transform. In this case, the imaging required for implementing optical coherence tomography (OCT), as already demonstrated in U.S. Pat. No. 5,321,501 for time domain OCT (TD OCT), is implemented by means of galvo scanners, which laterally deflect the measurement beam over the sample.

A first attempt at applying SS OCDR in optical biometry was described in [6] by F. Lexer, C. K. Hitzenberger, A. F. Fercher and M. Kulhavy. This solution showed that, in principle, it is possible to measure the intraocular distances within the eye; however, the measurement accuracy of 0.82 mm was much too inaccurate.

An improvement to this solution was disclosed by C. K. Hitzenberger, M. Kulhavy, F. Lexer, A. Baumgartner in [7]: "In-vivo intraocular ranging by wavelength tuning interferometry", SPIE [3251-6] 1998. Here a resolution of 0.15 mm was achieved, but this still does not meet the requirements. However, in order to restrict the residual errors of the determined IOL refraction to $\frac{1}{10}$ diopter, the measurement accuracy for the eye length must be less than 30 μm.

In particular, a problem for OCDR and OCT methods on moving samples, such as e.g. the human eye, is that the sample may move during the measurement which, as discussed by S. H. Yun et al. in [8]: (2004), OPTICS EXPRESS 2977, can significantly reduce and falsify the signals. Conventional approaches for rectifying the problem are complicated "tracking methods", in which the movement of the sample is detected and the measurement beam position is updated.

By way of example, such approaches for compensating typical movements of a couple hundred micrometers per second are described by Hammer et al. in [9] (2005), Journal of Biomedical Optics 10(2), 024038 and in US 2006/105903. A disadvantage of such approaches is that despite the great technical complexity this always results in some updating errors as a result of the finite latency time of such systems, particularly in the case of very fast eye movements, e.g. saccades.

In general, coherence-optical systems are very sensitive and so secondary light portions, i.e. disturbance signals as a result of reflections and echoes at disturbance points, such as fiber couplers, fiber ends or else optical elements, cannot be suppressed by reflection-reducing measures to the extent that there are no disturbing interferences in the measurement region. Such disturbance signals are created by the reflection of portions of the measurement or reference light at elements or structures within the interferometric measurement arrangement and superpose on the actual measurement signals, making it significantly more difficult to evaluate the latter. By way of example, in this context fiber couplers, fiber ends or connection points of interferometric measurement arrangements embodied using fiber optics or else optical elements such as filters, lenses, beamsplitters, attenuators, circulators or the like should be considered as disturbance points.

It is known that disturbance signals based on such disturbance points occur if the optical path differences of the light portions in the interferometer that are reflected at the disturbance points and interfere with one another are smaller than the sought-after double measurement depth of the OCT system (or lens spacing is smaller than measurement depth). Since the sensitivity of an OCT system can easily be more than 90 or 100 dB, it is generally not possible to reduce the light portions generated at the disturbance points directly. By way of example, a common anti-reflective measure only brings about an attenuation of the reflection by 20 . . . 30 dB. Although ever-higher demands on the return losses of fiber couplers led to the development of plug-in connections in the form of so-called HRL (high return loss) or APC (angled physical contact) plugs, in which the angled, anti-reflection-coated fiber ends reflect in the region of −40 to −60 dB; however, compared to the OCT sensitivities this still does not provide a sufficient disturbance reflection suppression.

The effects of such disturbance signals are explained in more detail below on the basis of two examples.

In this respect, FIG. 1 shows disturbance signals, created by reflections, in an interferometric measurement arrangement. The light beam 102 emanating from the illumination source 101 is split into a measurement beam 104 and a reference beam 105 by a fiber coupler 103. In the case illustrated here, the aforementioned light beams are routed in optical fibers (single mode fibers), which, in the following text, is not mentioned individually in each case. Parts of the measurement beam 104 are reflected by the eye 109 and by the fiber end 112 (denoted by an x) and reach a further fiber coupler 106 via fiber coupler 103 and fiber 114. There the superposition on the reference beam 105 takes place and the resultant interference signals are routed to the two detectors 107 and 108. After amplifying the differences between the interference signals in the amplifier 110, a data processing unit 111 generates the measurement result, here in the form of an A-scan 115. The measurement result is influenced by the fiber-end reflection 112 if the optical path lengths $L_1$ (from fiber coupler 103 to fiber coupler 106) and $L_2$ (from fiber coupler 103 to the fiber end 112, back to the fiber coupler 103 and on to fiber coupler 106 via fiber 114) have a difference that is less than the sought-after double measurement region $Z_{OCT}$. Under the condition that the magnitude of the path difference between the optical path lengths $L_1$ and $L_2$ is less than the sought-after double measurement region $Z_{OCT}$, there is interference between the two light portions and hence the measurement result is influenced.

In the following text, $Z_{OCT}$ should be defined as the one-sided measurement depth in the direction of the measurement beam before or after the zero point of the interferometer. This is half the optical path length of the light cycle up to the measurement object and back. The zero point of the interferometer is the imagined point on the measurement beam where the optical path lengths of the reference arm and the measurement arm have the same length. An optical path length is the effective path length, taking into account the refractive indices of the media through which the light travels.

In the interferometric measurement arrangement as per FIG. 2, the light is split and superposed, and the interference signals are detected and evaluated, as above, but the disturbance signal is created at the connection point 113 (denoted by an x) of the fiber 105 between fiber coupler 103 and fiber coupler 106. In this case, the connection point 113 influences the measurement result if the optical path lengths $L_1$ (from connection point 113 to fiber coupler 106) and $L_2$ (from connection point 113 to fiber coupler 103 and on to fiber coupler 106 via fiber 114) have a difference that is smaller than the sought-after double measurement region $Z_{OCT}$.

In order to prevent, or at least in order to minimize, the disturbance signals that are created at such disturbance points, the prior art only takes up partly effective, reflection-reducing measures, such as e.g. beamsplitters with oblique or anti-reflection-coated faces. Moreover, the cavities of the tunable light sources are selected such that measurement signals are only created in the sample arm and thus do not cause autocorrelation signals within the measurement region.

However, this can be avoided by suitably positioning the components and the reflection zones thereof, for example as per US 2007/0291277 A1. Then, influencing the measurement result is avoided if the following condition is satisfied:

$$|L_1 - L_2| > 2 * Z_{OCT} \tag{1}$$

with $L_1$: path length 1,
$L_2$: path length 2, and
$Z_{OCT}$: measurement region.

Furthermore, the prior art has disclosed that the illumination source must be matched to the sought-after measurement region $Z_{OCT}$ of the interferometric arrangement in order to allow optimum signal generation and the evaluation thereof. In particular, care has to be taken when using laser or semiconductor light sources, e.g. superluminescent diodes (SLEDs) as well, that those light sources are selected whose cavity has an optical path length that is greater than the sought-after measurement region $Z_{OCT}$ in order to prevent certain autocorrelation signal artifacts in the measurement region.

On the other hand, such a signal is deliberately generated in dual-beam interferometers in order, for example, to be able to establish movement-independent eye lengths.

In this respect, FIG. 3a shows a sketch of the principle of an interferometric dual-beam measurement arrangement. The light beam 202 emanating from the illumination source 201 is split into two partial beams 204 and 205 by the beamsplitter 216. Partial beam 204 is delayed by the value $L_R$ by a reflection element 217. If the eye length AL now corresponds to the delay length $L_R$, the delayed partial beam 204, after it was reflected on the cornea, interferes with the reflected, non-delayed partial beam 205 after the latter was reflected on the retina. A corresponding interference signal is created on the detector 207 and the data processing unit 211 generates the measurement result from said signal, here as an A-scan 115.

While a delayed light portion is used in the dual-beam interferometer for the measurement, the interferometric measurement arrangement as per FIG. 3b only wants measurement signals that result from the interference of reference light and light scattered back from the sample. Delayed light portions are unwanted in this example, although these can be emanated by the light source. In general, the delay of part of the light in coherent laser or semiconductor light sources is brought about by virtue of the fact that only some of the light cycling in the resonator is decoupled. The light portion that is routed back into the resonator at the decoupling point returns to the decoupling point after one cycle through the resonator. Thus, this produces light portions that are delayed by one or else more resonator cycles and are able to interfere with one another. In this example, the light beam 202 emanating from the light source 201 is split into a reference beam 204 and a measurement beam 205 at the fiber coupler 203. The light scattered back from the reflection element 217 and from the measurement object 209 is superposed in the fiber coupler 203. The created interference signals are measured by the spectrometer 218 and converted into the measurement result, in this case an A-scan 215, in the data processing unit 211. As described above using the dual-beam interferometer, delayed and non-delayed light portions can yield measurement signals if they impinge on structures with suitable spacing in the measurement object. Moreover, so-called autocorrelation signals may be created if the coherence length of the source is sufficiently large compared to the resonator length and, as a result thereof, light from different resonator cycles interferes with itself If the resonator length $L_R$ of the illumination source is now selected to be greater than the measurement region $Z_{OCT}$ thereof, it should be possible to assume that no disturbing interference signals are created.

Here, the resonator length $L_R$ should be understood to mean the optical path length that the light requires for one cycle in the illumination source. Hence, in the case of a ring laser, the resonator length $L_R$ corresponds to the length of the ring fiber. By contrast, in the case of a laser with a resonator, the resonator length $L_R$ is calculated from twice the length of the resonator because the light is only decoupled on one side and thus travels to and fro.

However, daily routine established that even if the two conditions are met, i.e. both the path differences of the disturbance-light portions created at a disturbance point and the cavity of the utilized light sources are selected to be greater than the sought-after measurement region $Z_{OCT}$, disturbance signals which adversely affect the evaluation of the measurement may, under certain circumstances, be created in the interferometric measurement arrangement. Here, this problem occurred particularly in the case of long-coherent swept-source-based OCDR systems and/or in the case of a large measurement region.

REFERENCES

[1] F. Lexer, C. K. Hitzenberger, A. F. Fercher, and M. Kulhavy; "Wavelength-tuning interferometry of intraocular distances"; APPLIED OPTICS Vol. 36, No. 25, 1997
[2] Chong Ch. et al.; "Large coherence length swept source for axial length measurement of the eye"; APPLIED OPTICS Vol. 48, No. 10, Apr. 1, 2009
[3] Reinstein D. et al.; "Very high frequency ultrasound analysis of a new phakik posterior chamber intra ocular lens in situ"
[4] Reinstein D. et al.; "Correlation of anterior chamber angle and Ciliarly Sulcus diameters with white-to-white corneal diameter in high myopes using Artemis VHF digital ultrasound"
[5] S. H. Yun et al.; "High-speed optical frequency-domain imaging", Optics Express 2003, 2953
[6] Lexer F. et al.; "Wavelength-tuning interferometry of intraocular distances"; APPLIED OPTICS Vol. 36 (1997), p. 6548-6553
[7] C. K. Hitzenberger, M. Kulhavy, F. Lexer, A. Baumgartner; "In-vivo intraocular ranging by wavelength tuning interferometry"; SPIE [3251-6] 1998
[8] S. H. Yun et al.; "Motion artifacts in optical coherence tomography with frequency-domain ranging", OPTICS EXPRESS 2004, 2977
[9] Hammer et al. (2005), Journal of Biomedical Optics 10(2), 024038

SUMMARY OF THE INVENTION

The present invention is based on the object of developing a device for swept source optical coherence domain reflectometry and tomography, which rectifies the known disadvantages of the solutions in the prior art and which is optimized in respect of the disturbance signals created by disturbance points present, with the device more particularly also being suitable for whole-eye scans of the human eye.

The present, optimized device for swept source optical coherence domain reflectometry and tomography, more particularly on the human eye, consisting of a tunable light source, matched to the sought-after measurement region $Z_{OCT}$, with a resonator length $L_R$, an interferometric measurement arrangement, a data capturing unit for capturing the light portions scattered back from the sample and a data processing unit, solves this object by virtue of the fact that the resonator length $L_R$ of the tunable light source is matched not only to the sought-after measurement region $Z_{OCT}$, but also to the entire interferometric measurement arrangement such that disturbance points present in the interferometric measurement arrangement cannot create disturbance signals in the sought-after measurement region $Z_{OCT}$.

The present invention relates to a device for swept source optical coherence domain reflectometry and tomography and is provided for whole-eye scans of the human eye, particularly in ophthalmology. However, in principle, the device can also be used in other technical fields in which distances should be measured with great precision by means of interferometry.

BRIEF DESCRIPTION OF THE DRAWINGS

In the following text, the invention will be described in more detail on the basis of exemplary embodiments. To this end.

DETAILED DESCRIPTION

Figure 1:
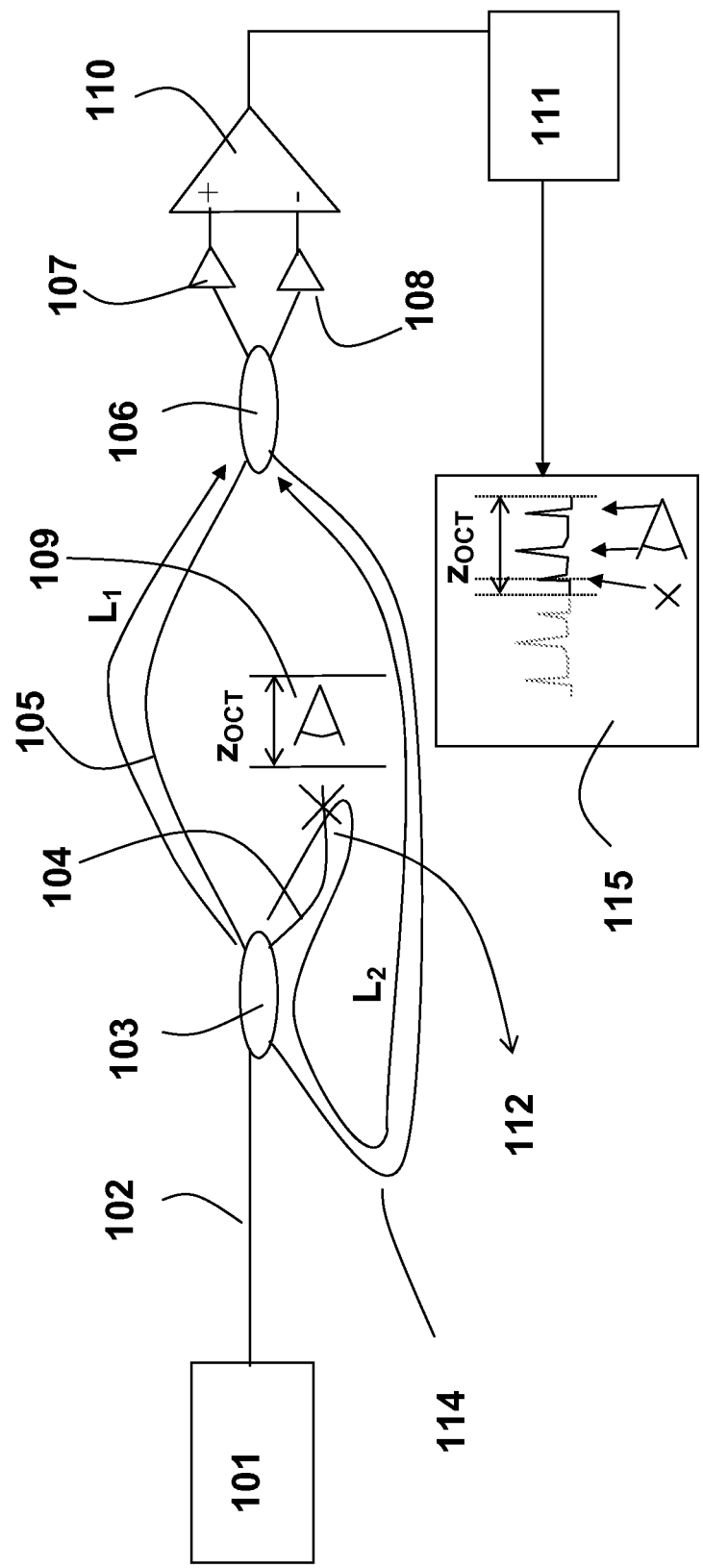
FIG. 1 is a representation of the principle of an interferometric measurement arrangement, with the disturbance signals that are created at one fiber end.

The optimized device according to the invention for swept source optical coherence domain reflectometry and tomography, more particularly on the human eye, includes a tunable light source, matched to the sought-after measurement region $Z_{OCT}$, with a resonator length $L_R$, an interferometric measurement arrangement, a data capturing unit for capturing the light portions scattered back from the sample and a data processing unit. Here, the resonator length $L_R$ of the tunable light source is matched not only to the sought-after measurement region $Z_{OCT}$, but also to the entire interferometric measurement arrangement such that disturbance points present in the interferometric measurement arrangement cannot create disturbance signals in the sought-after measurement region $Z_{OCT}$.

Here, laser or semiconductor light sources, such as e.g. superluminescent diodes (SLEDs) as well, are in particular suitable as tunable light sources. Femtosecond laser sources are also particularly well suited to this. The laser sources used as tunable light sources can comprise linear resonators or else be embodied as ring lasers.

By way of example, the utilized interferometers may be of the Michelson or Mach-Zehnder type. If use is made of Michelson interferometers and circulators in the source path, it is also possible to implement a balanced detection.

In order to match interferometer and tunable light source, it is advantageous if the resonator length $L_R$ is determined directly by means of an OCT assembly.

By way of example, to this end it is possible to introduce a test reflector, the position of which, and hence the path length $L_1$-$L_2$, is varied until disturbance signals occur. From the distance of the test reflector with respect to the reference plane of the reference light, it is possible to determine $n*L_R$.

Further displacement generates a distance-dependent, periodic occurrence of disturbance signals and hence a convenient generation of $L_R$. This makes it possible to verify that condition (1) is satisfied.

This procedure also shows that it is possible to implement OCT arrangements with periodic measurement zones; these are advantageous for applications in which the samples thereof do not only extend in one measurement region or absorb the light within one measurement region to below the sensitivity threshold such that no error signals can arrive from the next region.

When matching or selecting the tunable light source, particular care has to be taken that the following condition is satisfied for every disturbance point m in the interferometric measurement arrangement:

$$||L_{1,m}-L_{2,m}|-n*L_R|>2*Z_{OCT} \quad (2)$$

with $L_1$: the path length 1,
$L_2$: the path length 2,
$L_R$: the resonator length,
$Z_{OCT}$: the measurement region,
m: the number of all possible disturbance points, and
n: an integer variable>0.

If there are a plurality of disturbance points, care has to be taken that condition (2) is not only satisfied for each disturbance point individually, but rather for the entire OCT arrangement with all disturbance points. In particular, the influence the disturbance points have on one another should be taken into account here such that condition (2) must be satisfied for all possible path length differences. Thus, for example, in the case of an OCT arrangement with three disturbance points, the following possible wavelength differences that need to be taken into account emerge:

$$|L_{1,1}-L_{2,1}|, |L_{1,2}-L_{2,1}|, |L_{1,3}-L_{2,1}|$$

$$|L_{1,1}-L_{2,2}|, |L_{1,2}-L_{2,2}|, |L_{1,3}-L_{2,2}|$$

$$|L_{1,1}-L_{2,3}|, |L_{1,2}-L_{2,3}|, |L_{1,3}-L_{2,3}|$$

If condition (2) cannot or should not be satisfied and hence if disturbance signals are present in the measurement region, it could also be possible to mask the affected part of the measurement region. In particular, this is possible if there are zones in the measurement region, e.g. in the vitreous humor of an eye, in which no relevant signals are expected.

In the process, tunable light sources can also comprise a plurality of superposed resonator structures. However, this is uncritical for as long as condition (2) is satisfied for each individual structure.

Moreover, the tunable light source must also have a sufficient coherence length for even being able to produce interferences within the measurement region $Z_{OCT}$. The coherence length is sufficient if the signal attenuation in the measurement region is <20 dB, preferably <15 dB and particularly preferably <12 dB. The intensities of the light portions that interfere over paths $L_1$ and $L_2$ must satisfy the following condition:

$$R_4+R_2>R_r+\Sigma \quad (3)$$

with $R_1$: the attenuation of the light portion from the source to the detector via path $L_1$,
$R_2$: the attenuation of the light portion from the source to the detector via path $L_2$,
$R_r$: the attenuation of the reference light from the source to the detector, and
$\Sigma$: the sensitivity of the system.

Here, the attenuations $R_1$, $R_2$ and $R_r$ of the respective light portions are specified in dB. Herein, the sensitivity E of the system with the resultant reference light intensity is defined as that damping of the measurement light in the measurement object at which a signal can just still be detected.

Satisfying conditions (2) and (3) is important particularly for OCT systems that do not use balanced detection or in which the disturbance signals reach the beamsplitter or fiber coupler in front of the balanced detection via various inputs. This is because the prior art has disclosed that interference signals are suppressed by the balanced detection if these are only present at one input of the beamsplitter or fiber coupler in front of the balanced detection. Thus, for example, if an interferometric measurement arrangement as per FIG. 2 were also to obtain a disturbance signal as per FIG. 1 from the fiber end 112 in addition to the disturbance signal from the fiber connection 113, both disturbance signals could interfere with one another in the fiber coupler 103 and reach the fiber coupler 106 via fiber connection 114. However, this interference signal would be routed on in-phase to the detectors 107 and 108 by the fiber coupler 106 and would be suppressed by the difference amplifier 110.

Figure 4:
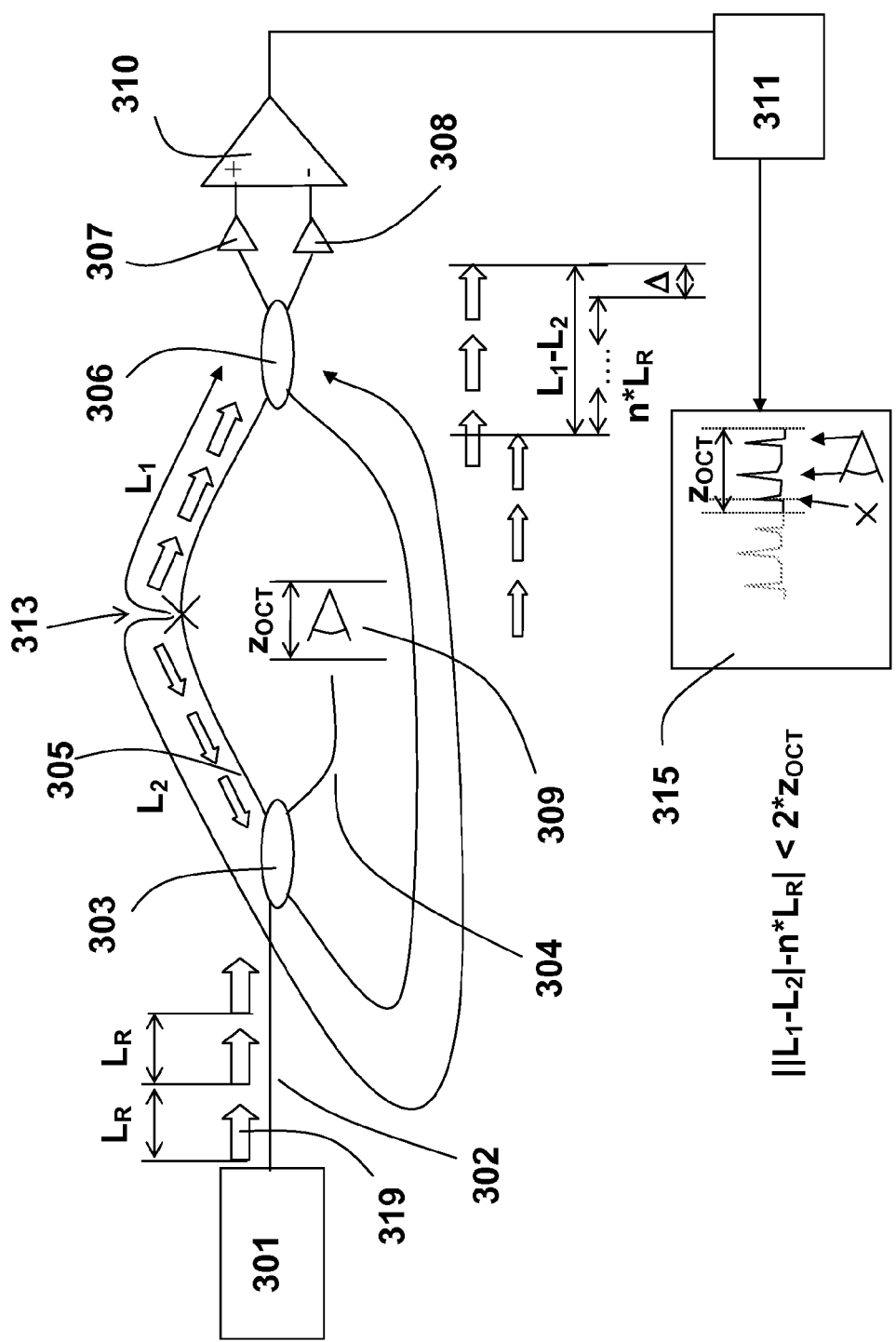

In this respect, FIG. 4 shows a sketch of the principle of a device according to the invention for swept source optical coherence domain reflectometry, with an illumination source matched to the interferometric measurement arrangement.

The light beam 302 emanating from the illumination source 301 is split into a measurement beam 304 and a reference beam 305 by the fiber coupler 303. While the reference beam 305 is directly imaged on the two detectors 307 and 308 via a further fiber coupler 306, the measurement beam 304 generates a depth scan of the eye 309, which depth scan is made to superpose on the reference beam 305 on the two detectors 307 and 308 via the fiber couplers 303 and 306 and routed via a difference amplifier 310 to a data processing unit 311, which generates the measurement signal therefrom as an A-scan 315. The two detectors 307 and 308 perform a so-called balanced detection of the actual interference signals $L_{Ref}$ (from the reference arm) and $L_{Mess}$ (from the measurement arm) arriving at the fiber coupler 306.

The reflection created at the fiber connection 313 (denoted by an x) produces two light portions with the path lengths $L_1$ and $L_2$. The fiber connection 313 constitutes the disturbance point m=1. The arrows denoted by reference sign 319 should in this case characterize the characteristic of the resonator cycle of the light beam 302 emitted by the illumination source 301 as a function of the resonator length $L_R$.

Although the reflection created at the fiber connection 313 could be suppressed or extinguished by using non-reciprocal elements such as e.g. Faraday isolators or circulators, this does not solve the underlying problem because disturbing reflections can in turn occur at the connection points thereof Irrespective thereof, such non-reciprocal elements are very expensive and may moreover have an adverse effect on the measurement signals, e.g. modifying the polarization modes.

Even if the magnitude of the path difference of the optical path lengths $L_1$ and $L_2$ is greater than the sought-after double measurement region $Z_{OCT}$, there may be interference between the two light portions and hence the measurement results may be influenced. This can only be reliably prevented by selecting the resonator length $L_R$ of the tunable light source 301 and matching it to the interferometric measurement arrangement such that the following condition is satisfied, ideally for every disturbance point m:

$$||L_{1,m}-L_{2,m}|-n*L_R|>2*Z_{OCT} \quad (2)$$

For practical reasons, equation (2) need not be satisfied for all potential disturbance points. Significant improvements in the signal also occur provided that equation (2) is satisfied for a main disturbance point, i.e. for at least one potential disturbance point. Thus, for example, it is feasible that the disturbance signals created at some disturbance points are either small enough or else occur in those zones in which no relevant signals are expected. Here, such disturbance points are referred to as non-potential disturbance points and need not necessarily satisfy condition (2). In particular, it is advantageous if remaining disturbance signals do not lie over the noise level of the OCT system by more than 10 dB.

Figure 5:
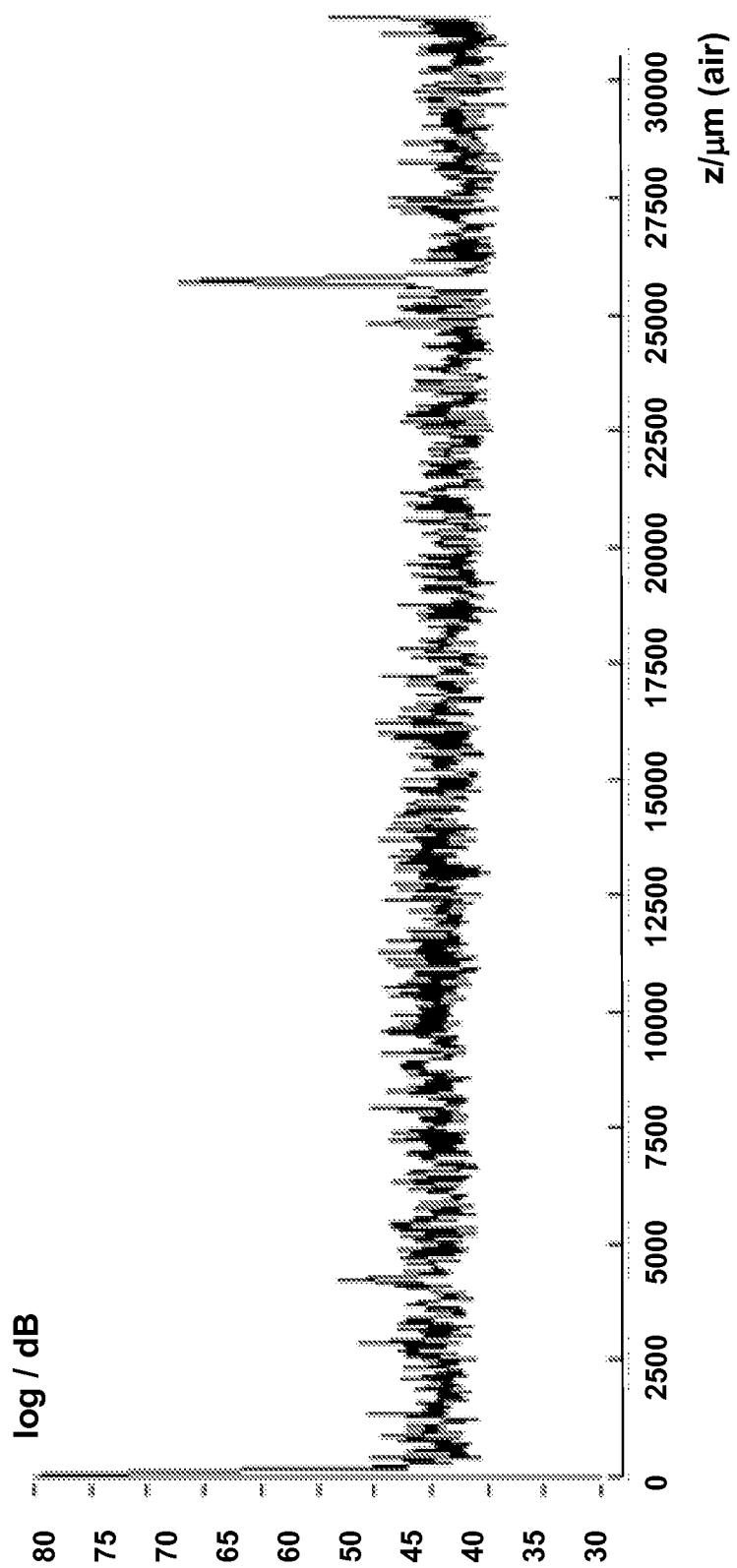
FIG. 5 depicts the measurement signal profile for an interferometric measurement arrangement according to the prior art.
Figure 6:
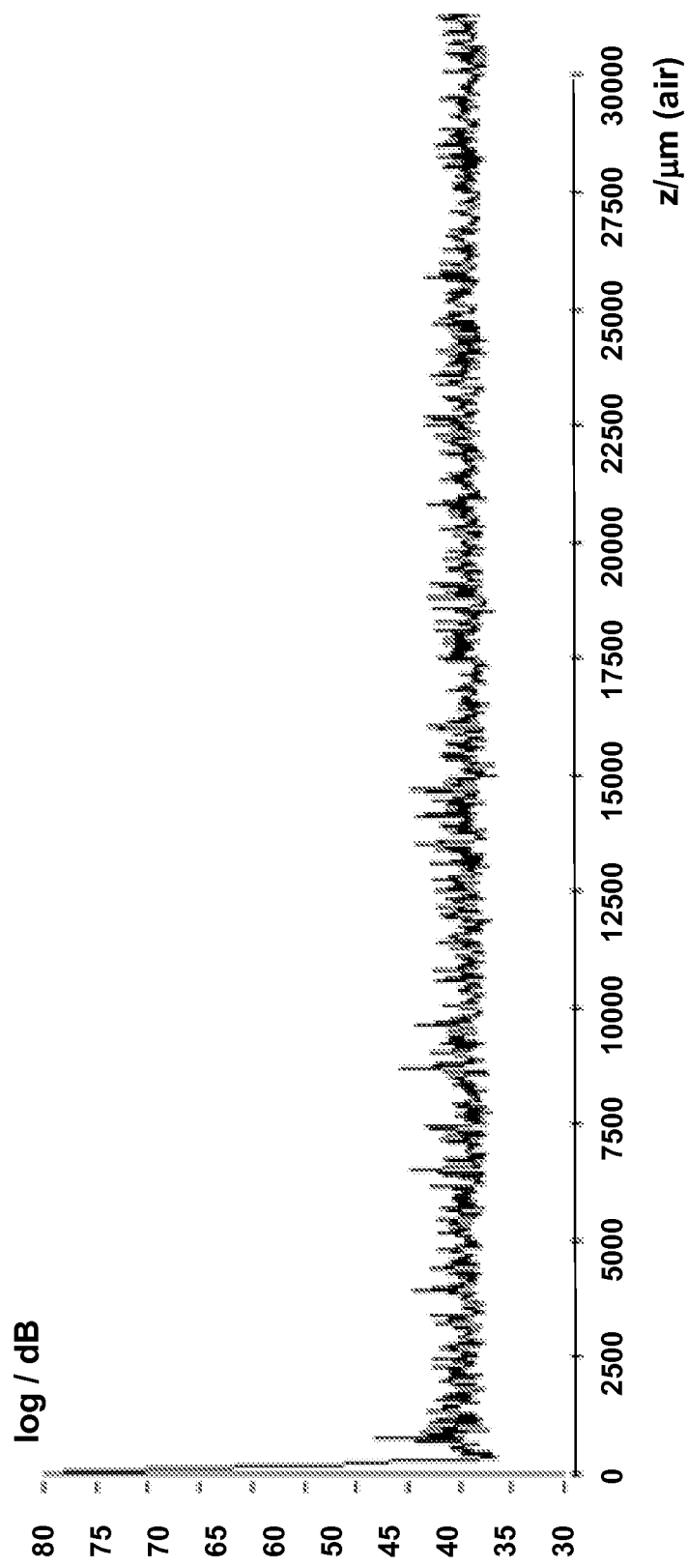
FIG. 6 depicts the measurement signal profile for a device according to the invention for swept source optical coherence domain reflectometry.

In order to clarify this, FIGS. 5 and 6 show measurement signal profiles from interferometric measurement arrangements.

FIG. 5 shows the measurement signal profile of an interferometric measurement arrangement according to the prior art, in which the resonator length $L_R$ of the tunable light source was not matched to the interferometric measurement arrangement. Accordingly, the creation of disturbance signals must be expected. In the measurement signal profile, this is highlighted by the intensity jump at a measurement depth of approximately 26 000 µm.

These artifacts in the form of the intensity jump can for example be reduced by recording background signals and subtracting the latter. The so-called background signals characterize disturbances of the measurement arrangement in the no-load state, i.e. when no measurement object is present.

Here, the artifact signals ultimately are interferences between light portions that originate from different resonator cycles of the light while the laser is still being tuned. Hence, in general, the phase relation between these light portions is not stable, which is why the artifact signals fluctuate and these then cannot be eliminated to a sufficient extent by subtracting the background.

In contrast thereto, FIG. 6 shows the measurement signal profile of a device according to the invention for swept source optical coherence domain reflectometry and tomography, in which condition (2) is satisfied for all disturbance points. Accordingly, the measurement signal profile has no intensity jumps that indicate a disturbance point.

In a particularly advantageous embodiment, the sought-after measurement region $Z_{OCT}$ of the interferometric measurement arrangement is up to 20 mm, particularly preferably up to 25 mm, which corresponds to a path length in air of 35 mm and 42 mm, respectively.

In a further example embodiment, use is made of tunable light sources with a long resonator length $L_R$, the resonator length $L_R$ preferably being $>10*Z_{OCT}$, particularly preferably $>40*Z_{OCT}$ because the mode structure of the light source becomes more expedient with increasing resonator length.

Condition (2) being satisfied should be explained below using example calculations. In this respect, the following conditions hold true: $Z_{OCT}=3$ cm.

Figure 2:
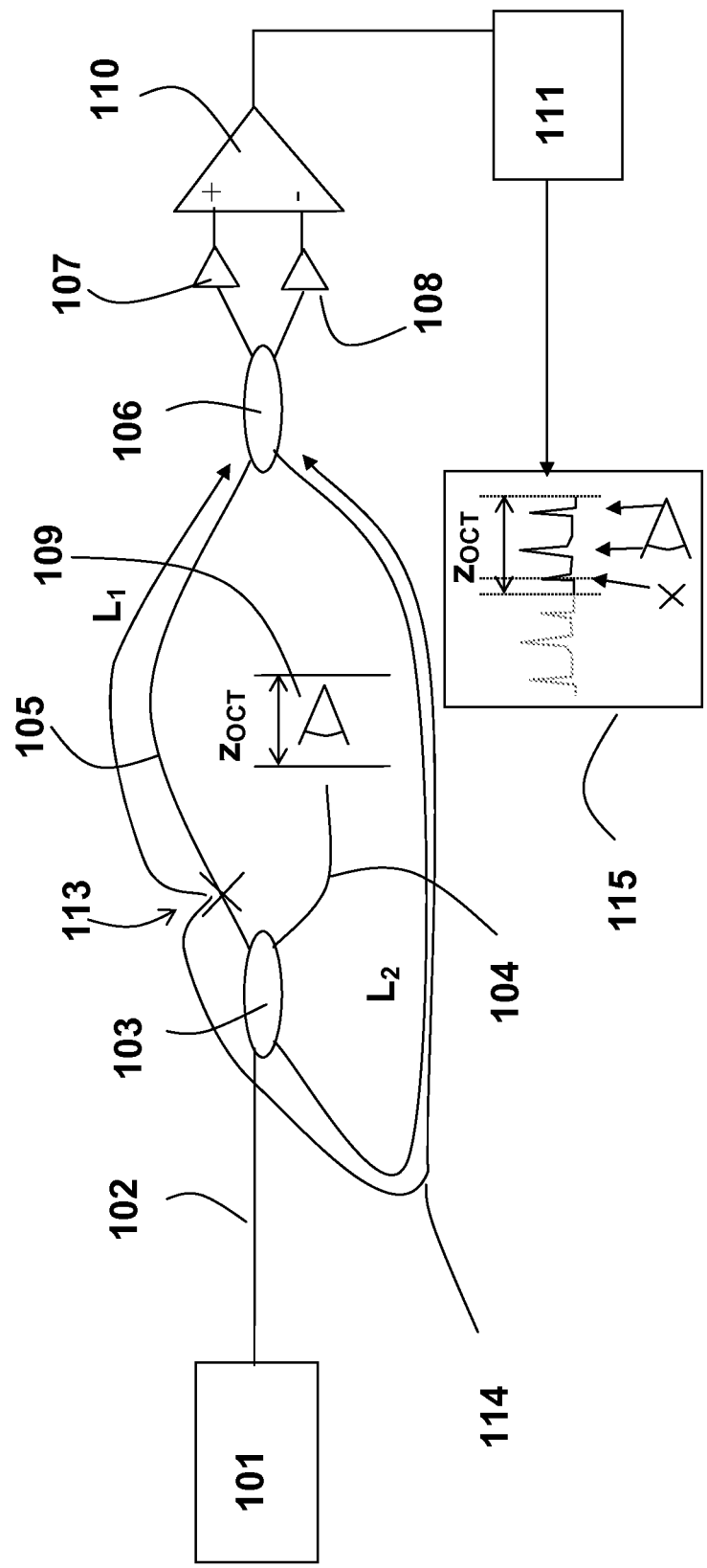
FIG. 2 is a representation of the principle of an interferometric measurement arrangement, with the disturbance signals that are created at a connection point of optical fibers, FIG. 3a schematically depicts the principle of an interferometric measurement arrangement using the dual-beam principle, FIG. 3b schematically depicts the principle of an interferometric measurement arrangement for SD-OCT in which the resonator length $L_R$ of the illumination source must be matched to the measurement region $Z_{OCT}$, FIG. 4 schematically depicts the principle of a device according to the invention for swept source optical coherence domain reflectometry, with an illumination source matched to the interferometric measurement arrangement.
Figure 3A:
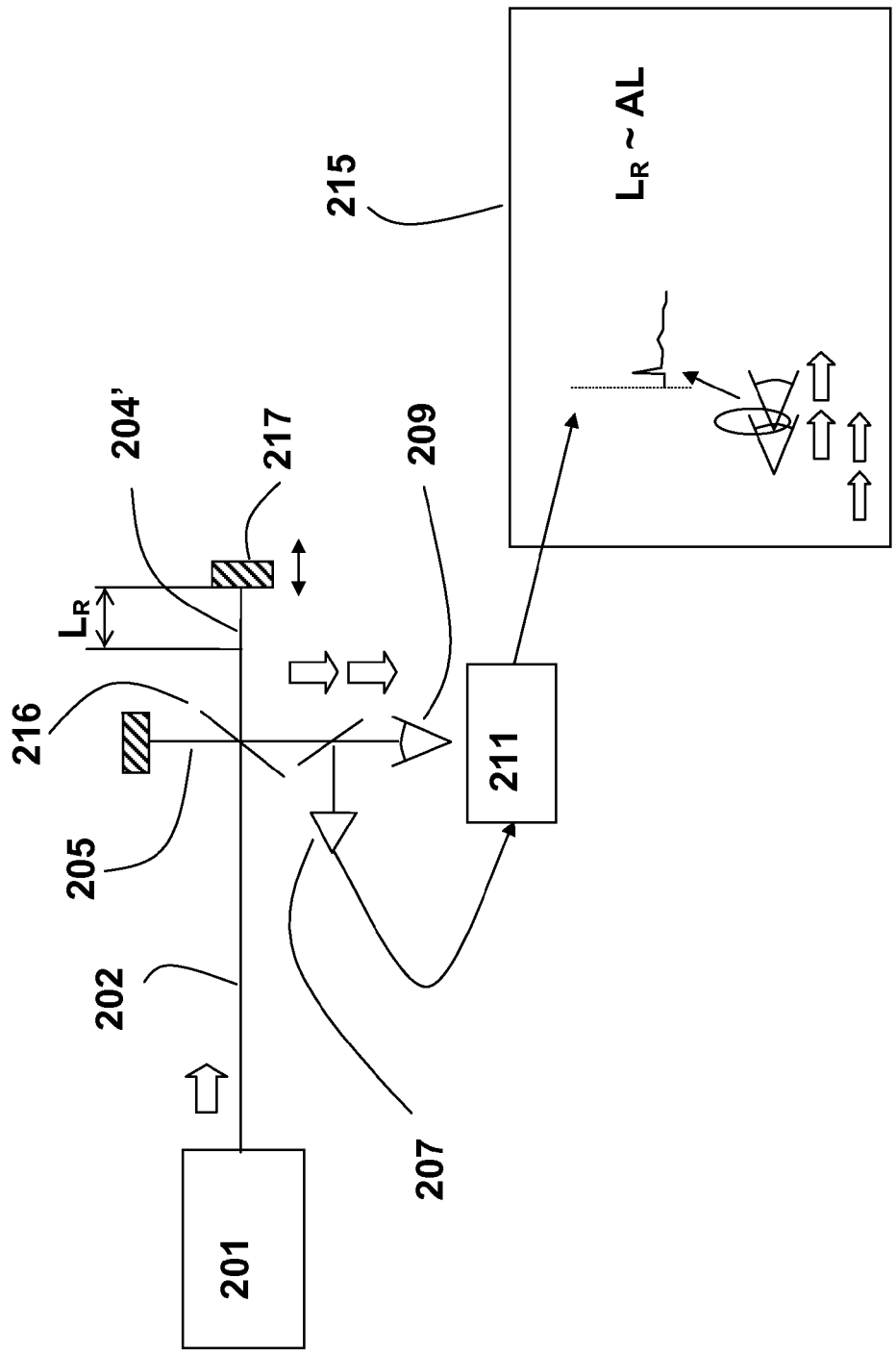
Figure 3B:
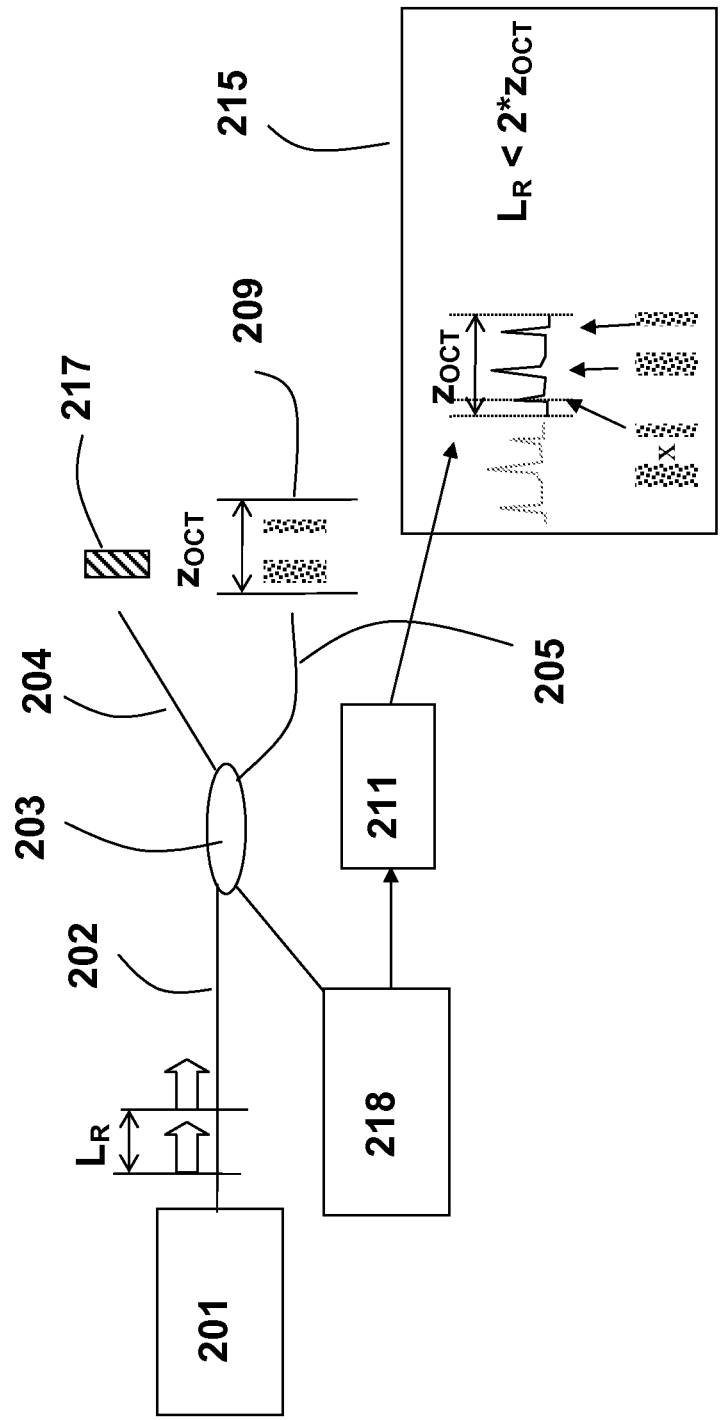

An OCT system as per FIG. 2 is assumed to have a sensitivity of $\Sigma=-110$ dB in the case of reference-light intensity set with $R_r=-17$ dB. An APC fiber connector in the reference arm creates a return reflection of $R_1=-60$ dB. There is no second disturbance reflection $R_2$ and the reflection from the fiber connector only interferes with the reference light. Condition (3) is satisfied with: $-40$ dB$>-127$ dB. The paths of the light via $L_1$ and $L_2$ are described in the above explanation in respect of FIG. 2. The path difference thereof now for example is assumed to be 102 cm.

If a tunable light source with a resonator length $L_R=50$ cm is used, condition (2) for n=2 is not satisfied because:

$$||L_{1,1}-L_{2,1}|-n*L_R|=|102 \text{ cm}|-2*50 \text{ cm}|=2<6 \text{ cm}.$$

Nor is condition (2) satisfied when a tunable light source with a resonator length $L_R=106$ cm is used because, for n=1, the following holds true:

$$||L_{1,1}-L_{2,1}|-n*L_R|=|102 \text{ cm}|-n*106 \text{ cm}|4<6 \text{ cm}.$$

However, condition (2) is satisfied if use is made of a tunable light source with a resonator length $L_R=45$ cm because then the following holds true for all n:

$$||L_{1,1}-L_{2,1}|-n*L_R|=|102 \text{ cm}|-n*45 \text{ cm}|>6 \text{ cm}.$$

In a further example embodiment of the optimized device, the data processing unit is designed such that whether condition (2) is satisfied by means of one-dimensional ray tracing using which the sought-after measurement region $Z_{OCT}$ of the interferometric measurement arrangement can be monitored. To this end, a one-dimensional ray tracing will be varied systematically until condition (2) is satisfied. Here, ray tracing constitutes a suitable solution for quickly and reliably monitoring whether condition (2) has been satisfied.

In a another example embodiment, the interferometric measurement arrangement is designed such that the distance to the measurement object can be varied. This is rendered possible by adjusting the path length of the reference light, as a result of which there is a change in the path difference $L_1$-$L_2$ for many disturbing reflections and condition (2) can be satisfied for many disturbing reflections.

Figure 7:
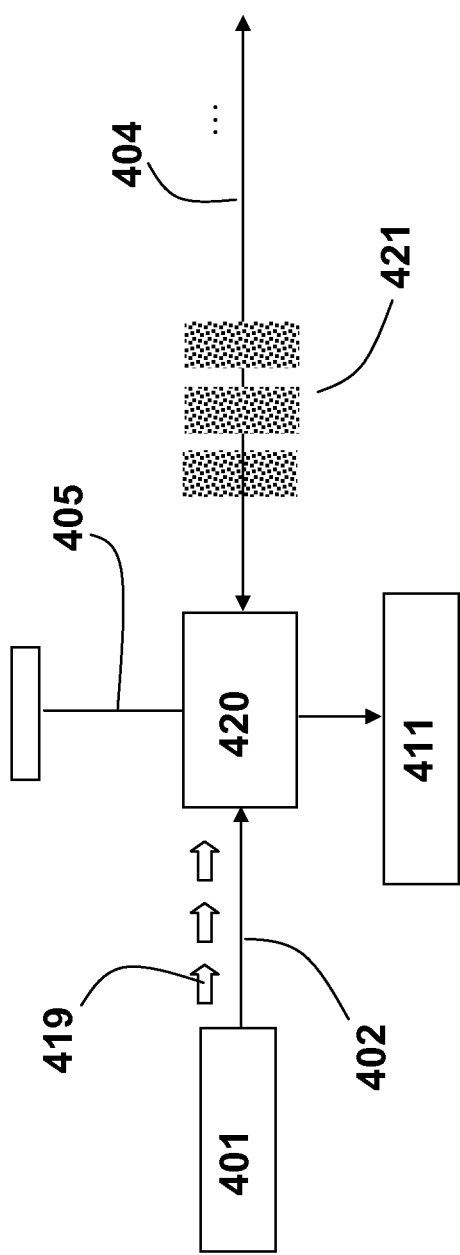
FIG. 7 depicts the resultant periodic measurement zones of a device according to the invention for swept source optical coherence domain reflectometry.

A further example embodiment is the use of periodic measurement zones. In this respect, FIG. 7 shows the resultant periodic measurement zones of a device according to the invention for swept source optical coherence domain reflectometry. The light beam 402 emanating from the illumination source 401 is split into a measurement beam 404 and a reference beam 405 by the interferometric measurement arrangement 420. While the reference beam 405 is imaged directly on a detector (not illustrated), the light portions delayed in the illumination source generate periodic repeating measurement zones 421.

This results from the fact that the interferometric measurement arrangement is designed such that mutually interfering sample and reference light portions originate from different cycles of the light in the resonator of the tunable light source. One measurement beam could, using such a measurement arrangement, provide a plurality of measurement points at large periodic distances from the OCT system, at which very precise measurements can be taken despite the large distance to the OCT system.

Furthermore, it is advantageous if the sample and reference arm of the interferometric measurement arrangement have a path length difference that is greater than the sought-after measurement region $Z_{OCT}$. Here, it is particularly advantageous to design the interferometric measurement region, or match it to the tunable light source, such that the path length difference between sample and reference arm is less than the sought-after measurement region $Z_{OCT}$ after subtracting an integer multiple of the resonator length $L_R$.

By way of example, if a test reflector is introduced into the collimated sample beam, the position thereof can be varied and, as a result, determined from the distance of the test reflector with respect to the reference plane of the reference light (n*$L_R$). If the test reflector is displaced further, the distance-dependent, periodic occurrence of the signal from test reflector allows the resonator length $L_R$ (double optical distance) to be determined in a convenient fashion. This procedure also demonstrates that it is possible to realize an OCT with periodic measurement zones.

An application is particularly advantageous if the sample only extends within one measurement region or if the light is absorbed below the sensitivity threshold within one measurement region such that no error signals can arrive from the next region.

In this context, it is likewise advantageous to design the data processing unit such that disturbance signals are detected and masked if condition (2) has not been satisfied.

The present invention provides a device for swept source optical coherence domain reflectometry and tomography which can rectify the known disadvantages of the solutions in the prior art and which is optimized in respect of the disturbance signals created by present disturbance points.

Here, the device according to the invention is provided for ophthalmology, more particularly for whole-eye scans of the human eye.

By matching the resonator length of the tunable light source not only to the sought-after measurement region but also to the entire interferometric measurement arrangement it is possible to ensure that disturbance points present in the measurement arrangement cannot create disturbance signals in the sought-after measurement region.

The invention claimed is:

1. An optimized device for swept source optical coherence domain reflectometry and tomography of structures including a human eye, comprising:
at least one tunable light source, matched to the sought-after measurement region $Z_{OCT}$, with a resonator length $L_R$;
an interferometric measurement arrangement;
a data capturing unit for capturing light portions scattered back from a sample and a data processing unit;
wherein the resonator length $L_R$ of the tunable light source is matched not only to the sought-after measurement region $Z_{OCT}$, but also to the entire interferometric measurement arrangement such that disturbance points present in the interferometric measurement arrangement cannot create disturbance signals in the sought-after measurement region $Z_{OCT}$;
wherein the resonator length $L_R$ of the tunable light source is selected such that the following condition is satisfied for at least one disturbance point m in the interfermetric measurement arrangement:

$$||L_{1,m}-L_{2,m}|-n*L_R|>2*Z_{OCT} \quad (2)$$

wherein $L_1$ represents a path length 1,
$L_2$ represents a path length 2,
$L_R$ represents the resonator length,
$Z_{OCT}$ represents the sought after measurement region,
m represents a number of all possible disturbance points, and
n represents an integer variable >0.

2. The optimized device as claimed in claim 1, wherein the tunable light source has a sufficient coherence length to produce interferences within the entire measurement region $Z_{OCT}$.

3. The optimized device as claimed in claim 1, wherein the tunable light source has a long resonator length $L_R$.

4. The optimized device as claimed in claim 3, wherein the resonator length $L_R$ of the tunable light source is about 0.5 m.

5. The optimized device as claimed in claim 4, wherein the resonator length $L_R$ of the tunable light source is about 1 m.

6. The optimized device as claimed in claim 1, wherein the resonator length $L_R$ of the tunable light source is selected such that the following condition is satisfied for every disturbance point m in the interferometric measurement arrangement:

$$||L_{1,m}-L_{2,m}|-n*L_R|>2*Z_{OCT} \quad (2).$$

7. The optimized device as claimed in claim 1, wherein matching the resonator length $L_R$ of the tunable light source to the interferometric measurement arrangement to satisfy the condition:

$$||L_{1,m}-L_{2,m}|-n*L_R|>2*Z_{OCT} \quad (2)$$

is of greatest importance for integer variables with n equal to 1 through 4.

8. The optimized device as claimed in claim 1, wherein the condition:

$$||L_{1,m}-L_{2,m}|-n*L_R|>2*Z_{OCT} \quad (2)$$

is satisfied for each individual structure for the tunable light source when the tunable light source includes a plurality of superposed resonator structures.

9. The optimized device as claimed in claim 1, wherein the intensities of light portions that interfere over paths $L_1$ and $L_2$ satisfy the following condition:

$$R_1+R_2>R_r+\Sigma \quad (3)$$

wherein $R_1$ represents an attenuation of the light portion from the light source to the detector via path $L_1$, $R_2$ represents an attenuation of the light portion from the light source to the detector via path $L_2$, $R_r$ represents an attenuation of the reference light from the light source to the detector, and $\Sigma$ represents a sensitivity of the system.

10. An optimized device for swept source optical coherence domain reflectometry and tomography of structures including a human eye, comprising:
at least one tunable light source, matched to the sought-after measurement region $Z_{OCT}$, with a resonator length $L_R$;
an interferometric measurement arrangement;
a data capturing unit for capturing light portions scattered back from a sample and a data processing unit;
wherein the resonator length $L_R$ of the tunable light source is matched not only to the sought-after measurement region $Z_{OCT}$, but also to the entire interferometric measurement arrangement such that disturbance points present in the interferometric measurement arrangement cannot create disturbance signals in the sought-after measurement region $Z_{OCT}$;
wherein the sought-after measurement region $Z_{OCT}$ of the interferometric measurement arrangement is up to about 35 mm in the human eye which corresponds to a path length in air of 49 mm.

11. The optimized device as claimed in claim 10, wherein the sought-after measurement region $Z_{OCT}$ of the interferometric measurement arrangement is up to about 40 mm, which corresponds to a path length in air of 56 mm.

12. The optimized device as claimed in claim 1, wherein the interferometric measurement arrangement is designed such that a distance from the eye can be varied until condition (2) is satisfied and there are no disturbance signals in the sought-after measurement region $Z_{OCT}$.

13. The optimized device as claimed in claim 1, wherein the interferometric measurement arrangement is structured such that mutually interfering sample and reference light portions originate from different cycles of light in a resonator of the tunable light source.

14. The optimized device as claimed in claim 1, wherein the interferometric measurement arrangement includes a sample arm and a reference arm that have a path length difference that is greater than the sought-after measurement region $Z_{OCT}$.

15. The optimized device as claimed in claim 1, wherein the data processing unit is designed such that whether condition (2) is satisfied is determined by application of one-dimensional ray tracing and the sought-after measurement region $Z_{OCT}$ of the interferometric measurement arrangement can be monitored using the one-dimensional ray tracing.

16. The optimized device as claimed in claim 1, wherein the data processing unit is designed such that background signals are recorded and subtracted from the measurement signals to reduce artifacts.

17. The optimized device as claimed in claim 1, wherein the data processing unit is designed such that disturbance signals are detected and masked if condition (2) has not been satisfied.

* * * * *